(12) United States Patent
Shimizu et al.

(10) Patent No.: US 7,646,117 B2
(45) Date of Patent: Jan. 12, 2010

(54) ACTUATOR AND ELECTRIC TOOTHBRUSH USING THE SAME

(75) Inventors: Hiroaki Shimizu, Hikone (JP);
Tomohiro Kunita, Hikone (JP);
Shinichi Taniguchi, Hikone (JP);
Suehisa Kishimoto, Hikone (JP);
Takahiro Nishinaka, Omihachiman (JP)

(73) Assignee: Matsushita Electric Works, Ltd., Osaka (JP)

( * ) Notice: Subject to any disclaimer, the term of this patent is extended or adjusted under 35 U.S.C. 154(b) by 26 days.

(21) Appl. No.: 12/003,251

(22) Filed: Dec. 21, 2007

(65) Prior Publication Data

US 2008/0258566 A1      Oct. 23, 2008

(30) Foreign Application Priority Data

Dec. 22, 2006    (JP)    ............................. 2006-346537

(51) Int. Cl.
*H02K 35/00* (2006.01)
(52) U.S. Cl. .................. 310/15; 310/12.01; 310/90; 15/22.1; 15/22.2; 15/28
(58) Field of Classification Search ............. 310/12–14, 310/15, 90; 15/22.1, 22.2, 28
See application file for complete search history.

(56) References Cited

U.S. PATENT DOCUMENTS

| 4,192,035 A | 3/1980 | Kuris |
| 5,406,664 A * | 4/1995 | Hukuba ........................ 15/22.1 |
| 7,120,960 B2 * | 10/2006 | Hilscher et al. ............... 15/22.1 |
| 2003/0131427 A1 | 7/2003 | Hilscher et al. |
| 2005/0125919 A1 | 6/2005 | Fattori |
| 2006/0158048 A1 * | 7/2006 | Kobayashi et al. ............ 310/12 |

FOREIGN PATENT DOCUMENTS

| EP | 0 510 940 | 10/1992 |
| EP | 1 684 401 | 7/2006 |
| GB | 2 317 555 | 4/1998 |
| RU | 2086176 | 8/1997 |
| RU | 2223787 | 2/2004 |
| SU | 1224882 | 4/1986 |
| WO | 02/062258 | 8/2002 |

* cited by examiner

*Primary Examiner*—Quyen Leung
*Assistant Examiner*—Leda Pham
(74) *Attorney, Agent, or Firm*—Bacon & Thomas, PLLC

(57) ABSTRACT

An actuator includes a shaft supported in such a manner as to make axial reciprocating movement or rotational reciprocating movement around longitudinal axis thereof, and an electricity conducting member for making contact with the shaft at a plurality of points on a circumferential surface of the shaft used as an electricity conducting path leading to other members. Further, an electric toothbrush includes the actuator as a drive power source for a brush body, and the brush body is adapted to be supplied with an electric current through the shaft.

13 Claims, 6 Drawing Sheets

ACTUATOR AND ELECTRIC TOOTHBRUSH USING THE SAME

FIELD OF THE INVENTION

The present invention relates to an actuator and an electric toothbrush using the actuator as a drive mechanism.

BACKGROUND OF THE INVENTION

There is known a toothbrush called an electric toothbrush, an ion toothbrush or an electronic toothbrush. This toothbrush is adapted to remove plague with potential gradient by allowing a weak current to flow through the body of a user to between a holder and a portion inserted into the user's mouth.

An electric toothbrush having such a function is disclosed in Japanese Patent No. 2560025. This electric toothbrush includes a shaft reciprocatingly driven in an axial direction thereof, a brush body attached to a tip end of the shaft and a terminal plate connected to an electric power source. The electric toothbrush is designed to supply electricity to the brush body through the shaft by bringing the terminal plate into contact with the shaft.

However, since the shaft makes sliding contact with the terminal plate during the course of reciprocating movement thereof, the shaft may be flexed when a brush of the brush body is pressed against the teeth or may be shaken when it makes reciprocating movement in an axial direction. This may change an electrical resistance in a sliding contact point between the shaft and the terminal plate, thereby posing a problem in that a great variation occurs in the electric current supplied.

SUMMARY OF THE INVENTION

In view of the foregoing, the present invention provides an actuator capable of stably supplying an electric current to a shaft axially reciprocating or rotationally reciprocating around a longitudinal axis thereof and also provides an electric toothbrush in which an electric current is stably supplied to a brush body by using the actuator.

In accordance with an aspect of the present invention, there is provided an actuator including: a shaft supported in such a manner as to make axial reciprocating movement or rotational reciprocating movement around longitudinal axis thereof; and an electricity conducting member for making contact with the shaft at a plurality of points on a circumferential surface of the shaft used as an electricity conducting path leading to other members. With such an actuator, since the electrical conducting member makes contact with the shaft at the plurality of points on the circumferential surface of the shaft, electrical stability is maintained by the contact at the remaining points even when the contact becomes unstable at one point.

The actuator may be a linear oscillating actuator. In this case, the actuator further includes a moving block provided in the shaft; and an electromagnetic block for, when applied with an alternating current, causing the moving block and the shaft to make the axial reciprocating movement or the rotational reciprocating movement around longitudinal axis of the shaft.

The electricity conducting member may be a bearing for supporting the shaft. Alternatively, the electricity conduction member may be a liquid or gel-like conducting agent disposed within a chamber into which the shaft is extended.

In accordance with an another aspect of the present invention, there is provided an electric toothbrush including the actuator described above as a drive power source for a brush body, the brush body adapted to be supplied with an electric current through the shaft. With such an electric toothbrush, the electric current is stably supplied to the brush body, so that plague can be effectively removed.

In accordance with the actuator of the present invention, an electric current is supplied to the shaft through the electrical conducting member that makes contact with the shaft at the plurality of points on the circumferential surface of the shaft. Therefore, even when an external force is applied to the shaft, occurrence of change in the electrical resistance between the shaft and the electricity conducting member is hardly found so that it is possible to supply a stable electric current to the shaft.

Further, even in case, the linear oscillating actuator is used as the actuator, which includes: the shaft, which can be driven at high speed, supported in such a manner as to make axial reciprocating movement or rotational reciprocating movement around the longitudinal axis thereof; the moving block provided in the shaft; and the electromagnetic block for, when applied with an alternating current, causing the moving block and the shaft to make the axial reciprocating movement or the rotational reciprocating movement around the longitudinal axis of the shaft, the electrical conducting member makes contact with the shaft at the plurality of points on the circumferential surface of the shaft. Accordingly, even when an external force is applied to the shaft, the electrical resistance between the high-speed driven shaft and the electrical conducting member is hardly varied. Therefore, an electric current can be stably supplied to the shaft to the shaft.

The electric toothbrush of the present invention also utilizes the electrical conducting member that contact with the shaft at the plurality of points on the circumferential surface of the shaft. Thus, a stable electric current can be supplied to the shaft, which makes the electric toothbrush remove plague effectively.

BRIEF DESCRIPTION OF THE DRAWINGS

The objects and features of the present invention will become apparent from the following description of embodiments given in conjunction with the accompanying drawings, in which.

DETAILED DESCRIPTION OF THE PREFERRED EMBODIMENTS

Figure 1:
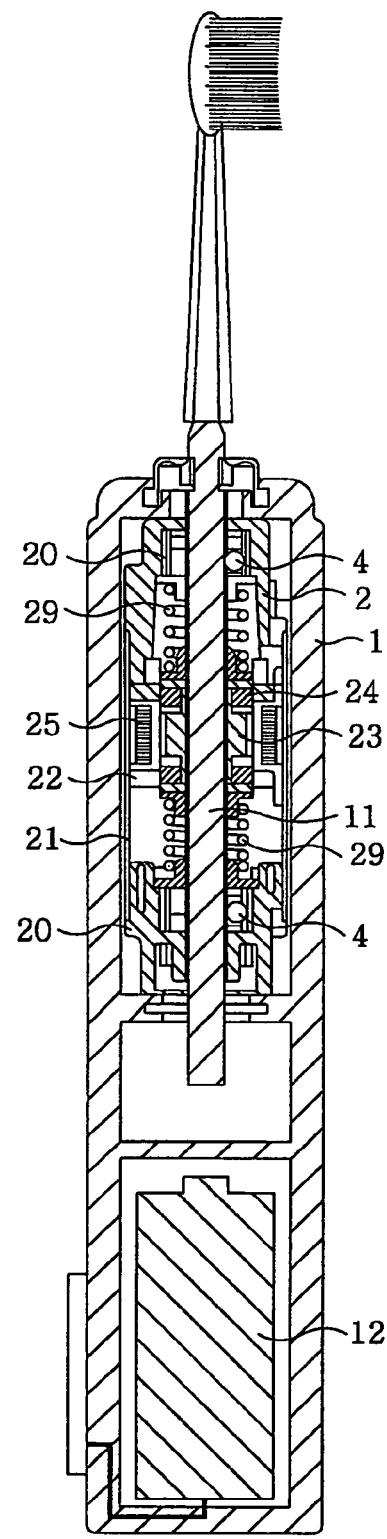
FIG. 1 is a longitudinal sectional view showing an electric toothbrush in accordance with an embodiment of the present invention.

Embodiments of the present invention will be described in detail with reference to the accompanying drawings which form a part hereof. FIG. 1 is a cross sectional view showing an electric toothbrush in accordance with one embodiment of the present invention. The electric toothbrush includes a cylindrical housing 1 that accommodates an actuator such as a linear oscillating actuator 2 and a battery 12 as an electric power source. A tip end portion of a shaft 11, which is reciprocatingly driven by the linear oscillating actuator 2 in an axial direction, protrudes from a tip end of the housing 1. A brush body 5 is detachably attached to the tip end portion of the shaft 11.

Figure 2:
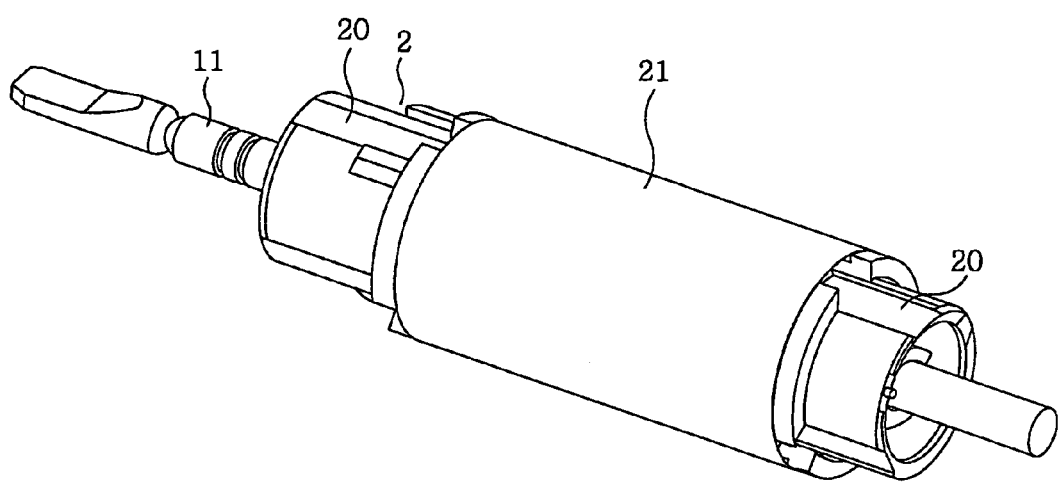
FIG. 2 is a perspective view illustrating a linear oscillating actuator of the electric toothbrush shown in FIG. 1.
Figure 3:
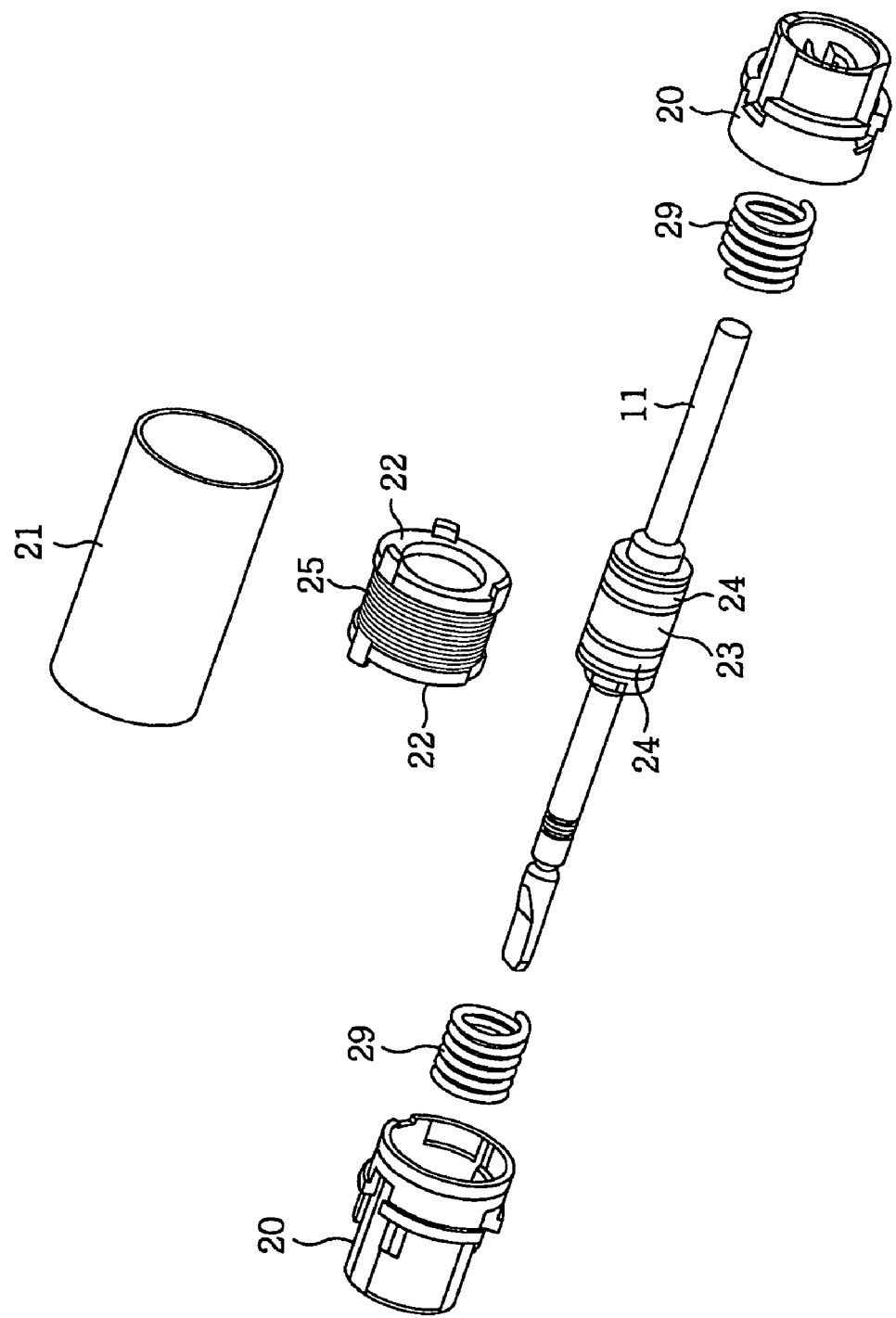
FIG. 3 is an exploded perspective view of the linear oscillating actuator shown in FIG. 2.
Figure 4:
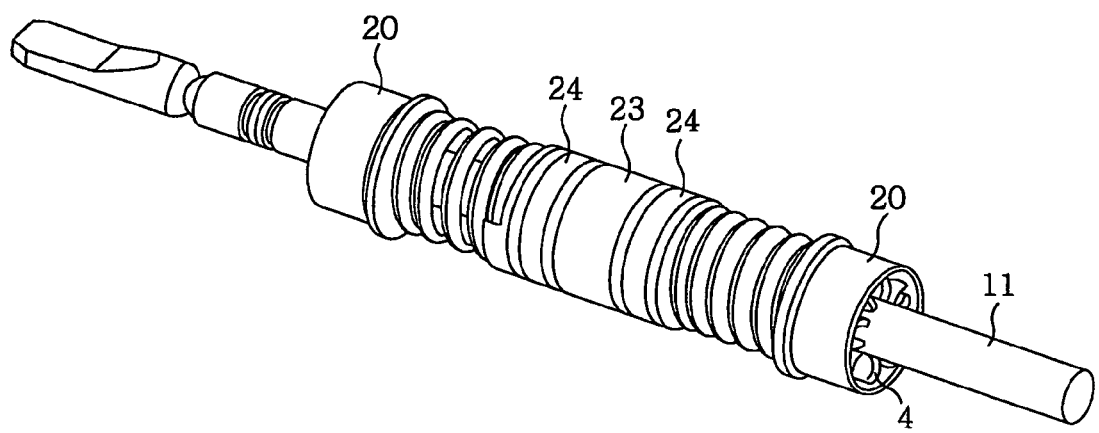
FIG. 4 is a perspective view of the linear oscillating actuator, with a case and an electromagnetic block thereof removed.

FIGS. 2 to 4 illustrate the linear oscillating actuator 2 in detail. A pair of shaft support portions 20 and 20 is disposed to support the shaft portions near the opposite ends of the shaft 11 such that the shaft 11 is axially slidable and rotatable around a longitudinal axis thereof. A cylindrical case 21 made of a magnetic material is disposed between the shaft support portions 20 and 20. Accommodated within the case 21 is a cylindrical electromagnetic block including a coil 25 and a pair of magnetic poles 22.

The shaft 11 is made of an electrically conductive material. A moving block having a permanent magnet 23 and a yoke 24 is fixedly secured to the middle portion of the shaft 11. The moving block is arranged in alignment with the inner circumference of the electromagnetic block. Coil springs 29 and 29 are respectively disposed between the moving block and the shaft support portions 20 and 20. The coil springs 29 and 29 are employed to ensure that the moving block and the shaft 11 serve as a spring vibration system.

If an electric current is applied to the coil 25 of the electromagnetic block, the moving block and the shaft 11 are driven in an axial direction by a magnetic attraction force or a magnetic repulsion force acting between the magnetic poles 22 and the permanent magnet 24 and the yoke 23. If an electric current is made to flow through the coil 25 in the reverse direction, the moving block and the shaft 11 are driven in the reverse direction. Thus, an alternating current is used as the applied current to the coil 25 so that the shaft 11 is reciprocatingly driven in the axial direction. At this time, stable reciprocating movement can be obtained by reciprocatingly driving the shaft 11 at a resonance frequency of the spring vibration system.

When the linear oscillating actuator 2 is accommodated within the housing 1 and the brush body 5 is connected to the tip end of the shaft 11, the shaft 11 of the linear oscillating actuator 2 is used as an electrical conducting path leading to the tip end portion of the brush body 5 in which a brush 50 is implanted.

In this connection, the shaft 11 is made to be reciprocatingly movable in the axial direction and rotatable around a longitudinal axis thereof. In view of this, an electrical conducting path leading to the shaft 11 is secured by using a bearing 4 disposed in the shaft support portion 20 located closer to the battery 12.

Figure 5:
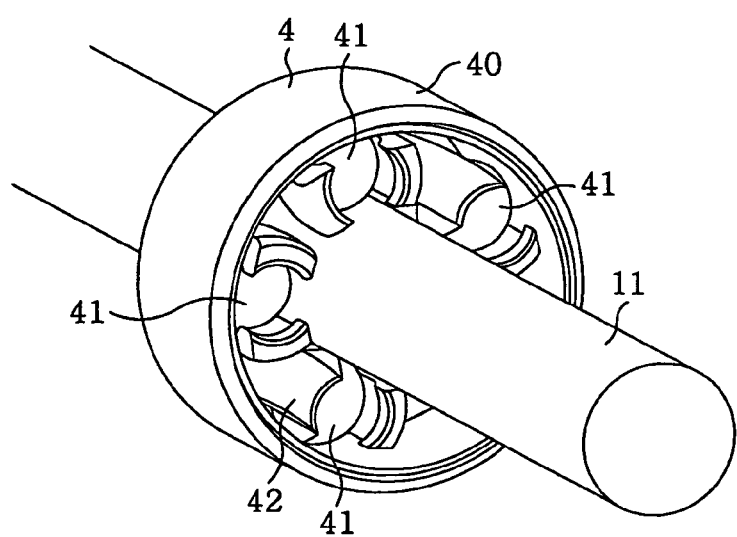
FIG. 5 is a perspective view showing a bearing of the linear oscillating actuator.
Figure 6:
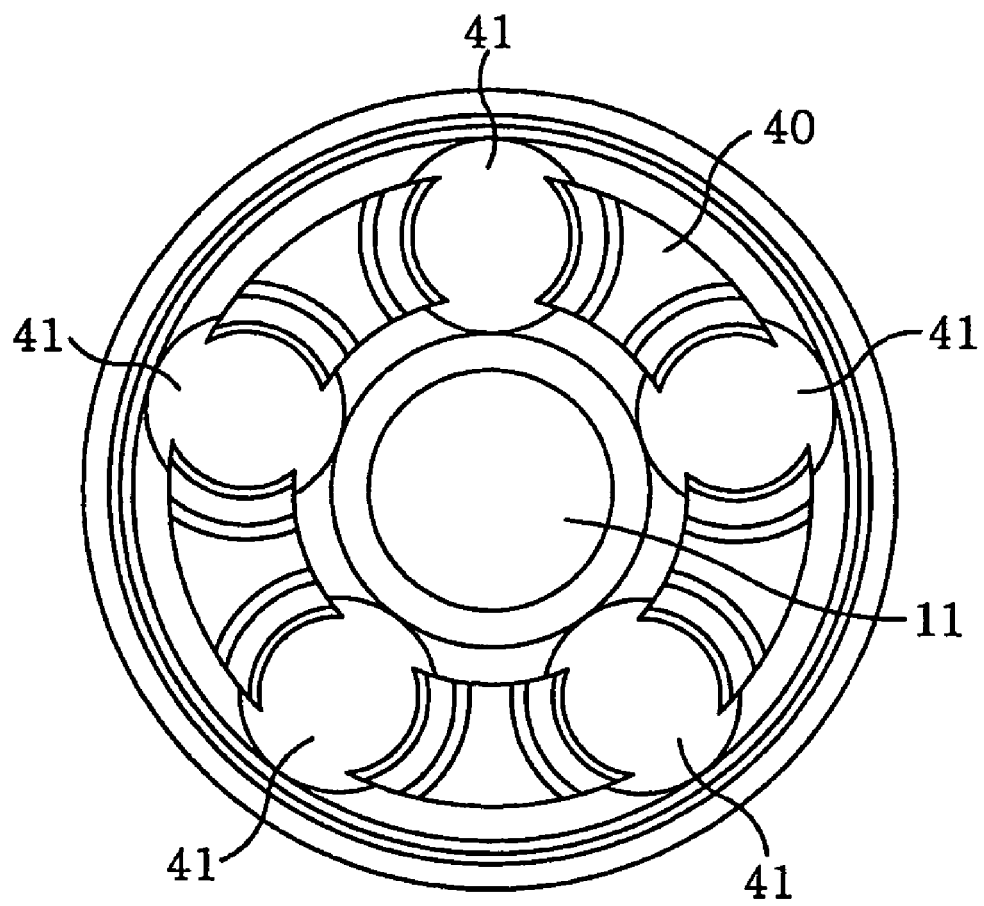
FIG. 6 is a front view showing the bearing of the linear oscillating actuator.

In other words, as shown in FIGS. 5 and 6, the bearing 4 includes an outer ring 40 and a plurality of steel balls 41 held within the inner circumference of the outer ring 40 by means of retainers 42. The outer ring 40 of the bearing 4 is connected to the battery 12 through a lead line. Since the steel balls 41 make contact with both the shaft 11 and the outer ring 40, an electric current can flow through the shaft 11. Further, since the steel balls 41 of the bearing 4 are provided in plural numbers, the electric current is supplied from the outer ring 40 to the shaft 11 through the steel balls 41 at a plurality of points on the outer circumference of the shaft 11.

Therefore, even when an external force is exerted on the shaft 11 and some of the steel balls 41 are separated from the shaft 11 to thereby increase an electrical resistance, the remaining steel balls 41 are kept in contact with the shaft 11. This eliminates a possibility that the electrical connection becomes unstable in the electricity supply part leading to the shaft 11.

The reason for supplying an electric current to the shaft 11 through the bearing 4 disposed in the shaft support portion 20 located closer to the battery 12 is that the length of the wiring lead line extending from the battery 12 to the bearing 4 can be shorten and that it is not required to pass the lead line through the portion of the linear oscillating actuator 2 in which the electromagnetic block is disposed. Alternatively, an electric current may be supplied to the shaft 11 through the bearing disposed in the shaft support portion 20 located closer to the brush body 5.

The brush body 5 has an internal electrical conducting path connected to the brush 50. The electrical conducting path is electrically connected to the shaft 11 at the contact surface with the shaft 11. A terminal plate 13 connected to the remaining pole of the battery 12 is disposed on the outer circumferential surface of the housing 1. When a user uses the electric toothbrush by gripping the housing 1 with one hand, the brush 50 is electrically connected to the terminal plate 13 through the body of the user.

Although there has been described, as the actuator, the linear oscillating actuator 2 that allows the shaft 11 to make reciprocating movement in the axial direction, the actuator may be of the type that allows the shaft 11 to make reciprocating rotational movement around its longitudinal axis. Furthermore, instead of the bearing 4 set forth above, it may be possible to use any type of bearing as long as it can make contact with the shaft 11 at a plurality of contact points. In case electrically conductive lubricating grease is applied to the bearing 4, the steel balls 41 may be non-conductive.

Figure 7:
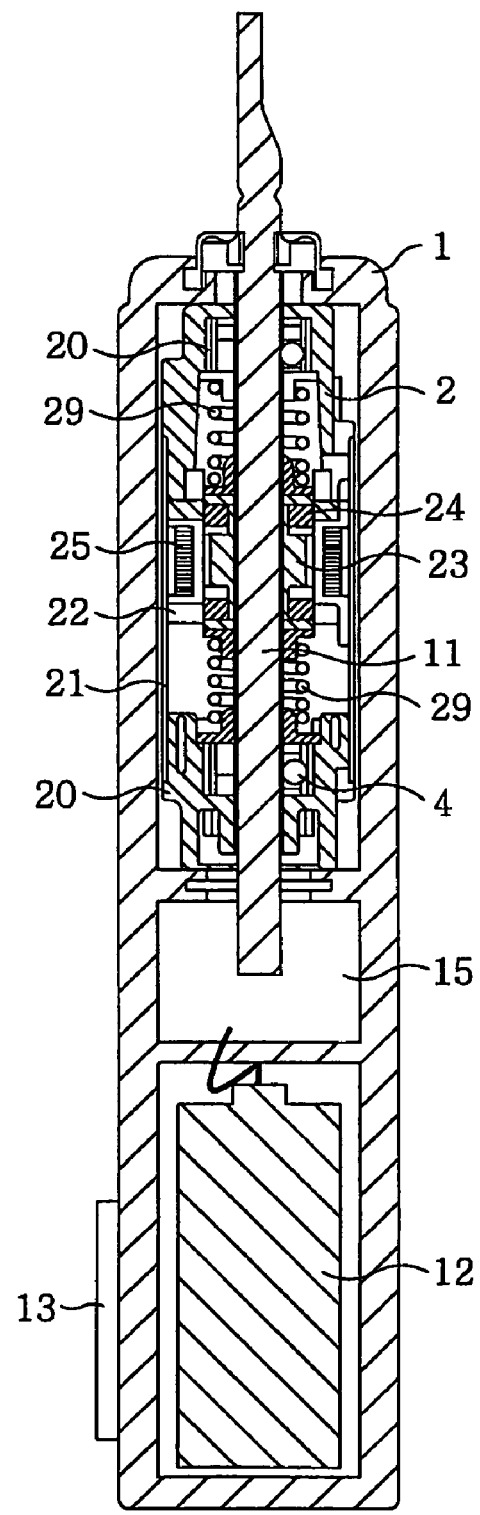
FIG. 7 is a longitudinal sectional view showing an electric toothbrush in accordance with another embodiment of the present invention.

FIG. 7 shows another embodiment of the present invention wherein an electricity-conducting chamber 15 filled with a liquid or gel-like conducting agent is provided in the housing 1 between the battery 12 and the linear oscillating actuator 2. One end portion of the shaft 11 that is reciprocatingly movable in the axial direction is positioned within the electricity-conducting chamber 15. Since a terminal connected at one end to the battery 12 protrudes into the electricity-conducting chamber 15 at the other end, the battery 12 is electrically connected to the shaft 11 through the conducting agent filled in the electricity-conducting chamber 15.

It is preferred that the conducting agent is impregnated into a sponge-like member which is disposed within the electricity-conducting chamber 15.

While the invention has been shown and described with respect to the embodiments, it will be understood by those skilled in the art that various changes and modifications may be made without departing from the scope of the invention as defined in the following claims.

What is claimed is:

1. An actuator, comprising:
 a shaft supported in such a manner as to make axial reciprocating movement or rotational reciprocating movement around a longitudinal axis thereof, a part of the shaft being disposed inside a housing accommodating therein the actuator and a tip end portion of the shaft being protruded from the housing for another member to be attached thereto; and
 an electrical conducting member that makes electrical contact with the part of the shaft at a plurality of points on a circumferential surface thereof, the shaft being used as an electrical conducting path leading to said another member.

2. The actuator of claim 1, wherein the actuator is a linear oscillating actuator, and further comprises:
   a moving block provided to the shaft; and
   an electromagnetic block for, when applied with an alternating current, causing the moving block and the shaft to make the axial reciprocating movement or the rotational reciprocating movement around the longitudinal axis of the shaft.

3. The actuator of claim 1, wherein the electrical conducting member is a bearing for supporting the shaft.

4. The actuator of claim 2, wherein the electrical conducting member is a bearing for supporting the shaft.

5. The actuator of claim 1, wherein the electrical conducting member is a liquid or gel-like conducting agent disposed within a chamber into which the shaft is extended.

6. The actuator of claim 2, wherein the electrical conducting member is a liquid or gel-like conducting agent disposed within a chamber into which the shaft is extended.

7. An electric toothbrush comprising:
   the actuator described in claim 1 as a drive power source for a brush body; and
   the brush body adapted to be supplied with an electric current through the shaft.

8. An electric toothbrush comprising:
   the actuator described in claim 2 as a drive power source for a brush body; and
   the brush body adapted to be supplied with an electric current through the shaft.

9. The actuator of claims 1, wherein the shaft is electrically connected to a battery disposed inside the housing through the electrical conducting member.

10. The actuator of claims 2, wherein the shaft is electrically connected to a battery disposed inside the housing through the electrical conducting member.

11. The actuator of claim 3, wherein the bearing includes a plurality of steel balls that make electrical contact with the shaft at the plurality of points.

12. The actuator of claim 4, wherein the bearing includes a plurality of steel balls that make electrical contact with the shaft at the plurality of points.

13. The actuator of claim 1, wherein the plurality of points is a plurality of discrete points such that the electrical conducting member makes electrical contact with the part of the shaft at a plurality of discrete points on a circumferential surface of the shaft.

\* \* \* \* \*